United States Patent [19]
Chun

[11] Patent Number: 6,027,340
[45] Date of Patent: Feb. 22, 2000

[54] ORTHODONTIC APPLIANCE FOR CORRECTING CLASS III MALOCCLUSION

[76] Inventor: Youn-Sic Chun, 6-1308,Keukdong APT.,Kwangjang-dong, Kwangjin-ku,Seoul, Rep. of Korea

[21] Appl. No.: 08/853,559

[22] Filed: May 8, 1997

[51] Int. Cl.$^7$ ..................................................... A61C 3/00
[52] U.S. Cl. ............................................................. 433/19
[58] Field of Search .................................. 435/6, 18, 19, 435/24

[56] References Cited

U.S. PATENT DOCUMENTS

| | | | |
|---|---|---|---|
| 2,259,160 | 10/1941 | Glaser | 433/19 |
| 3,798,773 | 3/1974 | Northcutt | 32/14 |
| 4,472,138 | 9/1984 | Howe | 433/19 |
| 4,618,324 | 10/1986 | Nord | 433/19 |
| 4,619,609 | 10/1986 | Clark | 433/6 |
| 4,708,646 | 11/1987 | Jasper | 433/19 |
| 5,120,218 | 6/1992 | Hanson | 433/19 |
| 5,324,196 | 6/1994 | Magill | 433/19 |
| 5,352,116 | 10/1994 | West | 433/19 |
| 5,678,991 | 10/1997 | Eganhouse | 433/19 |
| 5,697,781 | 12/1997 | Ellingson | 433/19 K |

OTHER PUBLICATIONS

"Twin Block Functional Therapy, Applications in Dentofacial Orthopaedics", William J. Clark, Mosby–Wolfe, 1995, pp.13–15; 133–34; 179–186.

Product Literature: "Orthodontic Laboratory Services," Pro Lab Services, Professional Positioners, Inc., Sep., 1989 (entire brochure).
Product Literature: "The Exclusive Ventral–Telescope," Pro Orthodontic Laboratory, Professional Positioners, Inc., Mar., 1993 (2 pages).
"Contemporary Orthodontics," Wm. R. Proffit, The C.V. Mosby Company, 1986, pp. 371, 376 and 384.
"Orthodontics Current Principles and Techniques," Thomas M. Graber, The C.V. Mosby Company, 1985, pp. 607–609.
Eganhouse, Gerald R., "Two–Piece Corrector for Class III Skeletal and Dental Malocclusions," Journal of Clinical Orthodontics, Apr. 1997.

Primary Examiner—Nicholas D. Lucchesi
Attorney, Agent, or Firm—Woodard, Emhardt, Naughton, Moriarty & McNett

[57] ABSTRACT

An orthodontic appliance comprising an upper splint defining a set of tooth sockets for secure but removable retention to the upper set of teeth, a lower splint defining a set of tooth sockets for secure but removable retention to the lower set of teeth, and a pair of elastic linkages which connect the upper and lower splints so as to force the maxilla forward. A traction bow with two ends adapted for releasable connection to the lower splint is provided with a sub bar fixed to its frontal center, and a hook is provided on each side of the upper splint. An elastic linkage is removably connected between each of the hooks and a clasp on an end of the sub bar. The sub bar is substantially shorter in length from end to end than the main bowed bar of the traction bow.

33 Claims, 6 Drawing Sheets

6,027,340

ORTHODONTIC APPLIANCE FOR CORRECTING CLASS III MALOCCLUSION

BACKGROUND OF THE INVENTION

This invention relates to orthodontic appliances, and particularly to an appliance for orthopedic treatment of the jaw bones to correct Class III malocclusion.

As illustrated in FIG. 1, human jaw bones comprise an upper jaw bone or maxilla 10 and a lower jaw bone or mandible 20, both pivotally linked for interrelated movement. An upper set of teeth 11 and a lower set of teeth 21 are formed on the respective jaw bones. Generally, as shown in FIG. 9, maxilla 110 is protracted a certain distance (B) anteriorly to mandible 120. A malocclusion where maxilla 10 is positioned posteriorly to mandible 11 a certain distance (A) as shown in FIG. 1 is classified as "Skeletal Class III Malocclusion."

The Skeletal Class III Malocclusion is caused by a relative undergrowth of maxilla 10 or overgrowth of mandible 20 or a combination of both. Orthopedic surgical treatment is applied for adults having excessive malocclusion while a camouflage treatment is available for a mild case. For children still growing, chin capsets restraining mandibular growth or traction devices protracting the maxilla are used for correcting malocclusion. The traction devices are designed for correcting discordance of jaw bones by restraining mandibular growth while inducing maxillary growth forward. Therefore, a traction device works most effectively in childhood when the maxilla actively grows causing high migration to the front.

FIG. 2 illustrates an embodiment of a known chin capset which comprises a head cap 1, chin cap 2 and traction bands 3 such as rubber bands to draw the chin cap back in the direction indicated by the arrow. FIG. 3 illustrates a known chin capset comprising a head cap 1, chin cap 2, traction bands 3 and forward-pulling bars 4 which pulls the maxilla forward relative to the mandible. Extraorally revealed head caps 1 and chin caps 2 make the chin capsets distracting and embarrassing for patients as well as inherently inconvenient to wear.

FIGS. 4 and 5 show an example of a maxilla traction device which was disclosed in Japanese Patent Publication No. 61-47098. This device comprises a cylinder 30 housing a spring (not shown), a movable rod 31 which linearly moves compressing the spring, a fixing rod 32 pivotally linked to an end of the cylinder 30, a first connector 34 pivotally linked at one of the movable rod 31 and united with a mandibular tooth 22, and a second connector 35 pivotally linked to an end of the fixing rod 32 and united with a maxillary tooth 12. This maxilla traction device is mounted on a maxillary tooth 12 and a mandibular tooth 22 and works to promote maxillary growth while restraining mandibular growth. Unlike the chin capset, it is mounted intraorally and therefore is more acceptable to patients. However, the maxilla traction device still has drawbacks. First, as first and second connectors 34 and 35 are mounted on a single maxillary and mandibular teeth respectively, the traction force is likely to be concentrated on the tooth causing damage on it. Therefore, another treatment is likely to be required after correcting the malocclusion. Second, its construction makes it inconvenient for a patient to put the device on and take it off for cleaning.

Other examples of orthodontic devices for correcting malocclusion are found in the following patents:

| Pat. No. | Inventor | Issue Date |
| --- | --- | --- |
| 3,798,773 | Northcutt | Mar. 25, 1974 |
| 4,619,609 | Clark | Oct. 28, 1986 |
| 4,708,646 | Jasper | Nov. 24, 1987 |
| 5,120,218 | Hanson | Jun. 9, 1992 |
| 5,352,116 | West | Oct. 4, 1994 |

FIG. 7 of U.S. Pat. No. 4,708,646 to Jasper illustrates the use of a pushing force for correction of underbite, and FIG. 8 of that patent illustrates the use of a pushing force between two splints for the correction of overbite. A device of the type shown in FIG. 8 has been made with acrylic molded over an impression of a patient's teeth so as to form a rigid splint conducive to a snap fit onto the patient's teeth. This device is ordinarily secured to the patient's teeth with a bonding agent applied by the patient's orthodontist.

U.S. Pat. No. 4,619,609 to Clark discloses a facebow having an inner bow and an outer bow and a forwardly projecting labial hook secured thereto for combined extraoral and intermaxillary traction, and also discloses complementary upper and lower bite blocks with angled pressure surfaces. Treatment of Class II malocclusion with the traction mechanism and/or bite blocks is described in some detail, and bite blocks having oppositely directed pressure surfaces to those described for Class II treatment are mentioned for the treatment of selected Class III malocclusions. The disclosed facebow's outer bow extends outside the patient's cheeks, where it is attached to headgear worn by the patient.

Retention of bite blocks can be problematic with traction applied, as noted by Clark in *Twin Block Functional Therapy* (Mosby-Wolfe, 1995), on page 134. In a chapter of that book devoted to the treatment of Class III malocclusion, Clark suggests a reverse pull facial mask for use with reverse Twin Blocks to apply an additional component of orthopedic force to advance the maxilla. Unlike the facebow of the Clark patent and a similar facebow discussed elsewhere in the Clark book in the context of Class II malocclusion, the reverse pull facial mask has no inner bow; elastic traction is applied only between the upper Twin Block and an extraoral bowed bar spanning the width of the patient's face. That bar and the outer bow of the Clark patent are highly visible and are aesthetically and otherwise undesirable to many patients, particularly as used with the necessary supporting headgear.

It is a general object of the present invention to provide improved methods and devices for treating Class III malocclusion.

It is another object of the present invention to provide an improved Class III orthodontic appliance which is intraorally mountable and thus less noticeable, consequently more acceptable to the patient, and ultimately more conducive to proper wear and desired results.

Another object of the present invention is to provide an improved Class III appliance which produces uniform traction force to the sets of teeth on the upper and lower jaws.

It is still another object of the present invention to provide a Class III appliance which is easy for a patient to put on and take off.

SUMMARY OF THE INVENTION

In order to achieve the above-stated objects, the orthodontic appliance of the present invention comprises an upper splint mounted on the upper set of teeth, a lower splint mounted on the lower set of teeth, and an elastic linkage which connects the upper and lower splints so as to force the maxilla forward. For holding the elastic linkage, a traction bow having two ends connected to the lower splint and a sub bar fixed at the frontal center of the traction bow with clasps is provided along with a pair of hooks each fixed at respective sides of the upper splint. One end of the elastic linkage is fastened at one clasp of the sub bar and the other end is fastened at one of the hooks. With an orthodontic appliance according to this invention, the patient has a more positive attitude due to the intraorally mounted appliance, and possible damage to teeth is avoided because the traction force is evenly distributed to maxilla dentition.

These and other objects and advantages of the present invention will be more apparent upon reading the following detailed description in conjunction with the accompanying drawings.

DETAILED DESCRIPTION OF THE PREFERRED EMBODIMENT

Figure 1:
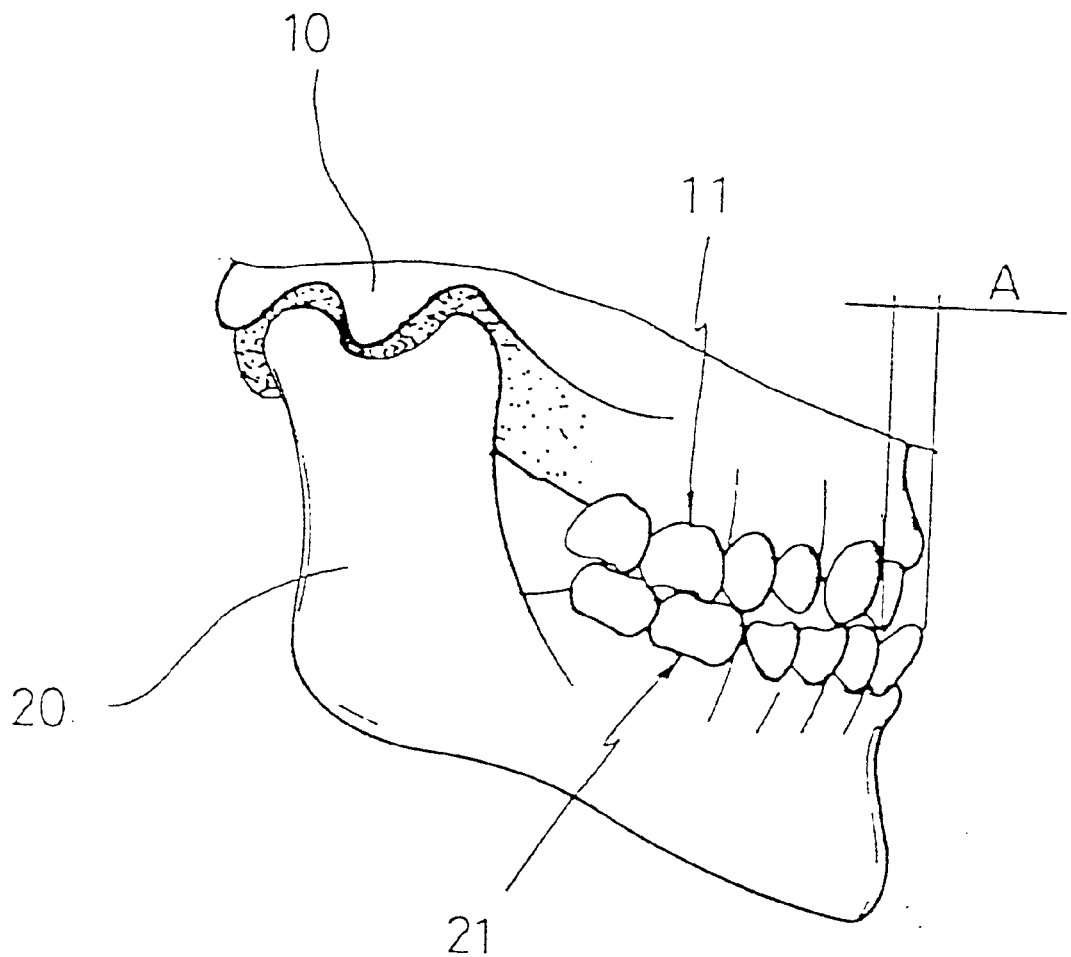
FIG. 1 is a side view of a set of jaws illustrating malocclusion.
Figure 2:
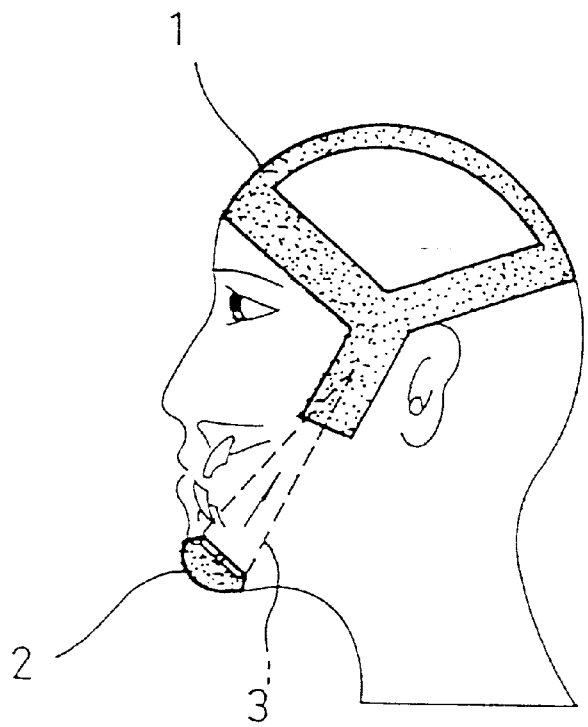
FIGS. 2 and 3 are side views of prior art devices.
Figure 3:
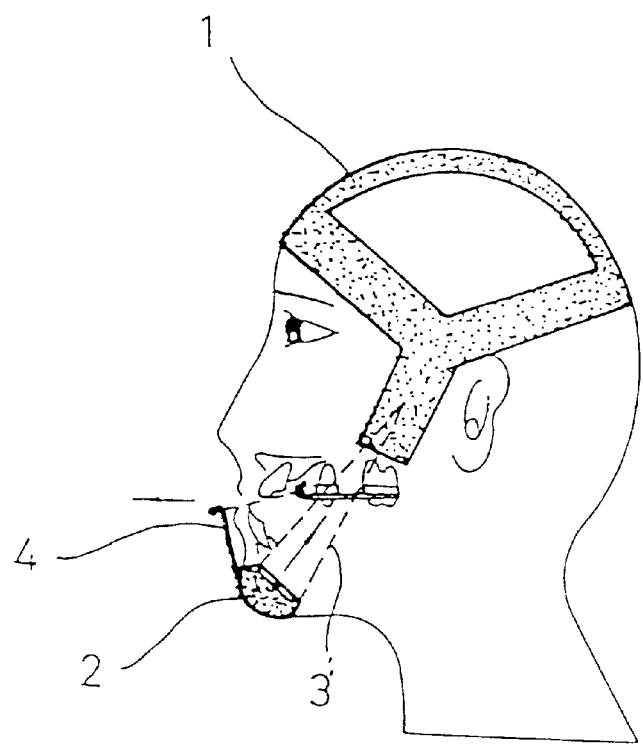
Figure 4:
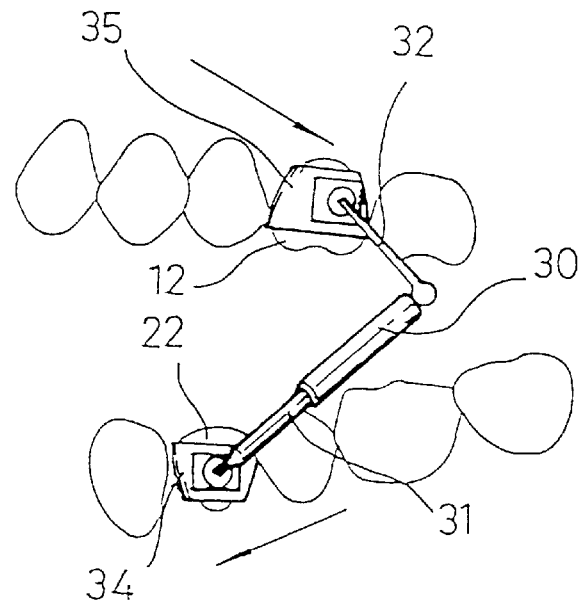
FIG. 4 shows another prior art device.
Figure 5:
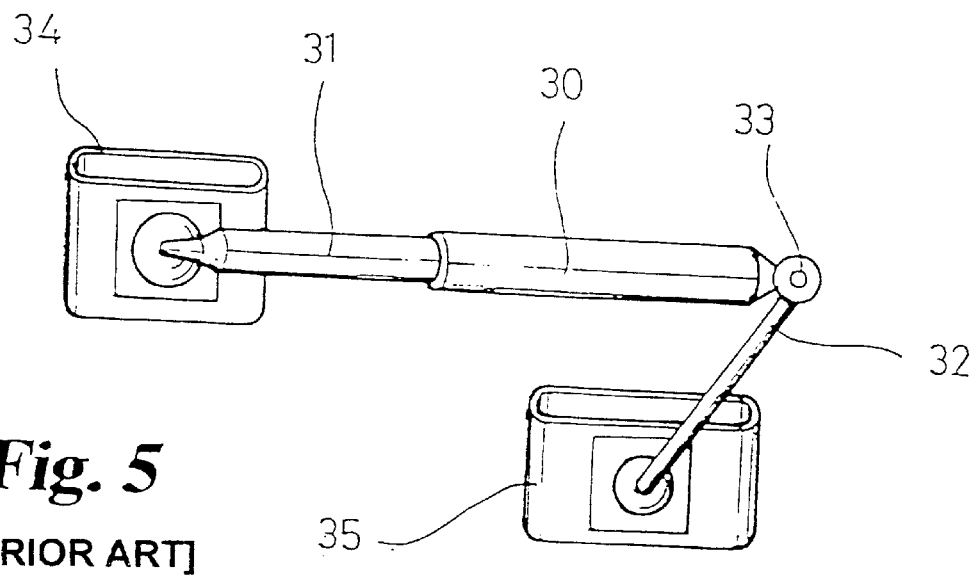
FIG. 5 is an enlarged view of the prior art device shown in FIG. 4.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

Figure 6:
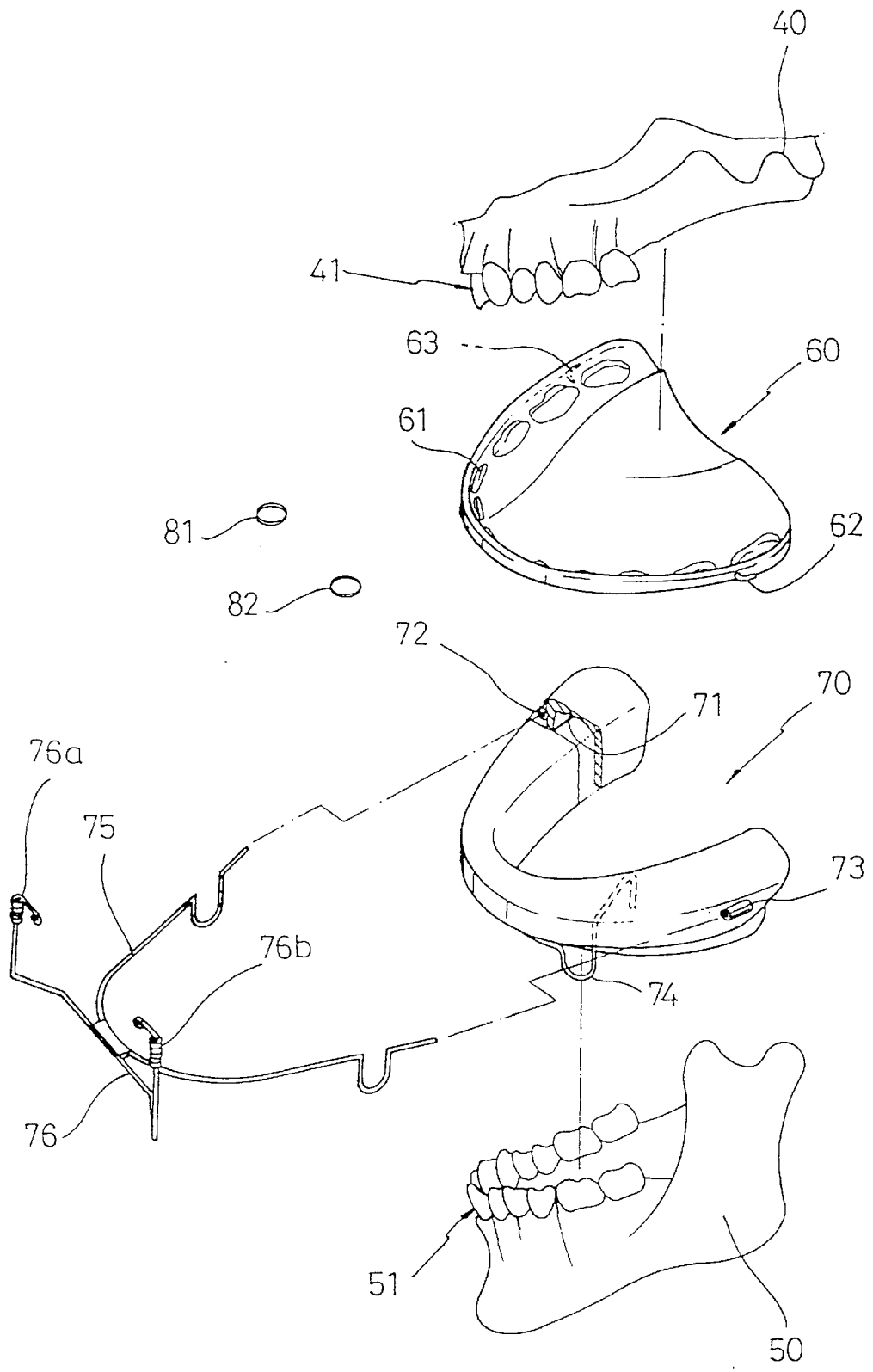
FIG. 6 is a perspective view of an embodiment of a Class III correction appliance according to the present invention.

Referring to FIG. 6, which shows an exploded view of a Class III appliance according to the present invention, the appliance comprises an upper splint 60 having a set of grooves or tooth sockets 61 to accommodate the upper set of teeth 41 of the maxilla 40, a lower splint 70 having a set of grooves or tooth sockets 71 to accommodate the lower set of teeth 51 of the mandible 50, and elastic linkages 81 and 82 which link upper and lower splints 60 and 70 to force upper splint 60 forward. The upper and lower splints 60 and 70 are preferably formed so as to fill interdental space so that the splints 60 and 70 remain in good retention to the sets of teeth when traction force is applied by the elastic linkages 81 and 82. The upper splint is also preferably formed so as to cover the patient's palatal surface, thereby aiding maxillary protraction and maximizing retention. A bow 75 with both ends connected to the lower splint 70, a sub bar 76 connected to the frontal center of the bow 75 and a pair of traction hooks 62 and 63 each fixed at respective edges of the upper splint 60 are provided so that the elastic linkages 81 and 82 are connected between the traction hooks 62 and 63 and the sub bar 76. Stainless steel is a suitable material for the traction bow; alternatively, the bow may be made of other materials available for a conventional facebow.

The bow 75 is positioned along the outer rim of the lower splint 70 with its ends detachably inserted into the connecting tubes 72 and 73 provided on the side wall at the posterior edge of the lower splint 70. In the preferred embodiment, the tubes 72 and 73 are the only point of contact between the bow and the lower splint. Hasps or hooks 76a and 76b are formed on the ends of the sub bar 76 to hang the elastic linkages 81 and 82. A reinforcer 74 is provided in the lower splint 70 for preventing deformation and strengthening the retention of the lower splint to the lower set of teeth 51. The elastic linkages 81 and 82 are preferably rubber bands. Springs can be used in place of the rubber bands.

Figure 8:
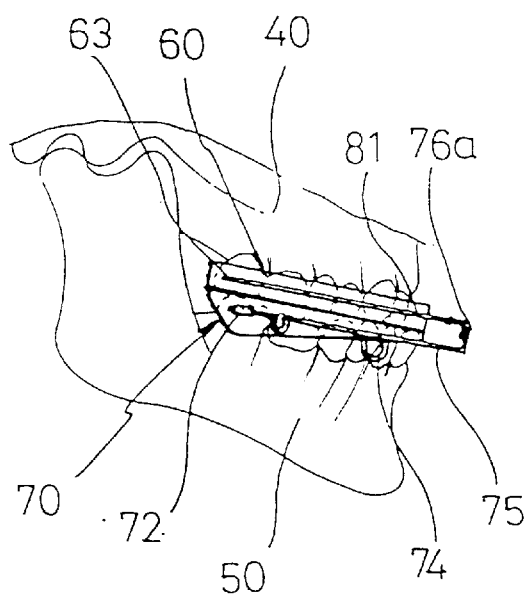
FIG. 8 is a side view showing the jaws closed with the correction appliance of the present invention mounted thereon.
Figure 9:
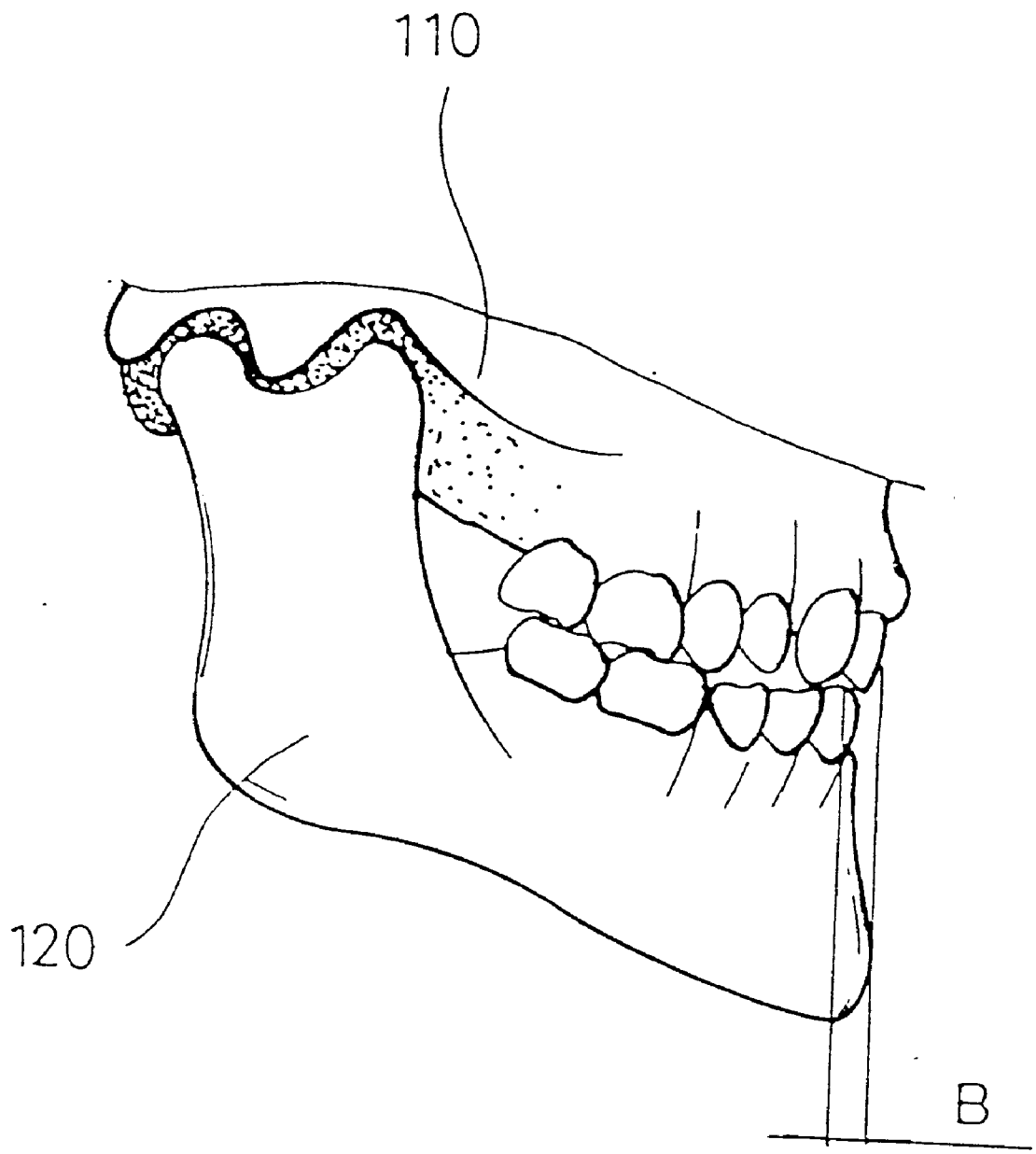
FIG. 9 is a side view of a set of jaws after correction.

In use, the upper splint 60 is positioned above the lower splint 70 and the elastic linkages 81 and 82 are respectively attached between the hasps 76a and 76b of the sub bar 76 and traction hooks 62 and 63. Then, the upper and lower splints 60 and 70 are put on the upper and lower sets of teeth 41 and 51. Wearing the device as shown in FIG. 8, the patient experiences a traction force produced by the elastic linkages 81 and 82 and applied to the maxilla 40 at a predetermined angle below the contact plane of the upper and lower splints 60 and 70. An angle of about 20° has been found suitable. A different direction of the traction force may be provided in accordance with an individual patient's maxillary status by positioning the tubes 72 and 73 at a different angle on the lower splint or providing a bend in bow 75. The bow is constructed so as to resist flexing in response to the traction force developed during use.

Figure 7:
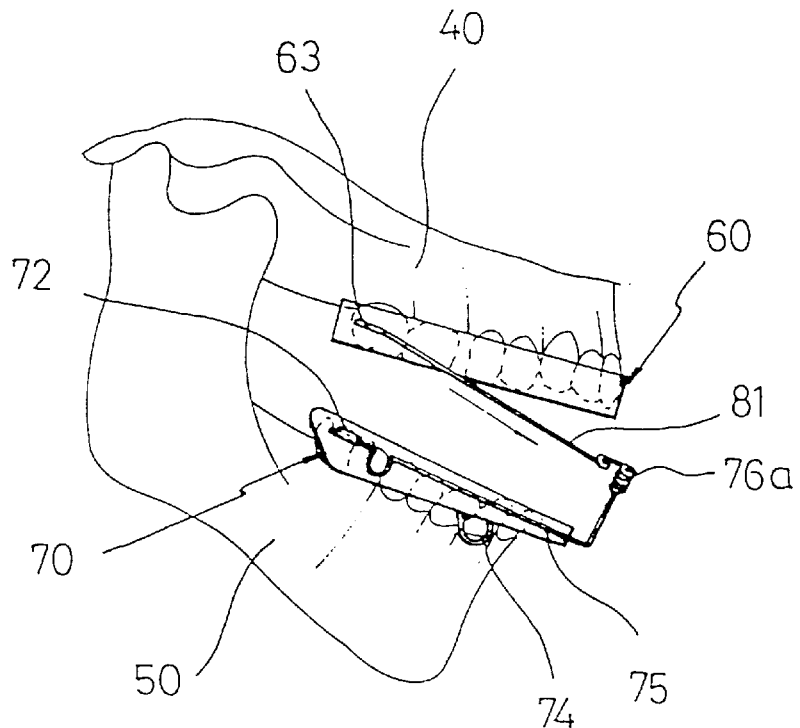
FIG. 7 is a side view of a set of jaws opened with the correction appliance of the present invention mounted thereon.

FIGS. 7 and 8 illustrate that the upper and lower splints 60 and 70 and elastic linkages 81 and 82 can be intraorally mounted while the sub bar 76 is slightly exposed to the outside of the mouth. The restoring power of the elastic linkages 81 and 82 applies outwardly to maxilla 40 forcing its growth forward and applies inwardly to the mandible 50 retarding mandibular growth.

With the embodiments described above, it is possible to shorten the required period of treatment by avoiding the patient's unwillingness to wear the device. During use, the present invention provides uniform traction force to the upper and lower sets of teeth through the upper and lower splints 60 and 70, protecting the teeth from damage from concentrated or uneven traction force. Better oral hygiene is also facilitated by the ease with which the appliance can be put on and taken off by the patient.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An orthodontic appliance for the treatment of a Class III malocclusion, comprising:
    an upper splint retentive to an upper set of teeth and attachable thereto and removable therefrom by a patient;
    a lower splint retentive to a lower set of teeth and attachable thereto and removable therefrom by a patient; and
    means for exerting a forward pulling force on said upper splint relative to said lower splint, said means including at least one elastic traction element attached between said upper and lower splints.

2. The orthodontic appliance of claim 1, further comprising:
   a pair of traction hooks fixed to said upper and splint;
   a bowed bar having two ends connected to said lower splint and a sub bar fixed to the frontal center of said bowed bar and having two laterally spaced ends,
   wherein said at least one elastic traction element comprises at least one elastic traction element attached between each of said traction hooks on said upper splint and an end of said sub bar.

3. The orthodontic appliance of claim 2, wherein said elastic traction elements are rubber bands.

4. The orthodontic appliance of claim 3, wherein each traction hook is fixed to a posterior portion of said upper splint and each end of said bowed bar is connected to a posterior portion of said lower splint.

5. The orthodontic appliance of claim 1, wherein each said elastic traction element is a rubber band.

6. The orthodontic appliance of claim 1, wherein each said elastic traction element is attached to a posterior portion of said upper splint and extends forward therefrom at an angle inferior to the occlusal plane of the patient's upper set of teeth when said appliance is worn by the patient.

7. An orthodontic appliance for the treatment of a Class III malocclusion, comprising:
   an upper splint retentive to an upper set of teeth and attachable thereto and removable therefrom by a patient;
   a lower splint retentive to a lower set of teeth and attachable thereto and removable therefrom by a patient;
   traction means including a traction bow mounted on said lower splint for pulling said upper splint forward relative to said lower splint.

8. The orthodontic appliance of claim 7, wherein said upper splint includes a pair of traction hooks fixed thereon;
   wherein said traction bow includes a curved frontal center portion, two ends connected to said lower splint, and a sub bar fixed to said frontal center portion and having two laterally spaced ends; and
   wherein said traction means further includes an elastic traction element removably connected between each of said traction hooks and an end of said sub bar.

9. The orthodontic appliance of claim 8, wherein said traction bow further includes a hook on each end of said sub bar.

10. The orthodontic appliance of claim 9, wherein said laterally spaced ends of said sub bar extend above said frontal center portion of said traction bow.

11. The orthodontic appliance of claim 10, wherein said splints each include a plurality of sockets for individual teeth and filling interdental space.

12. The orthodontic appliance of claim 11, wherein said splints each include a buccal sidewall at least on a posterior portion thereof, and wherein said traction hooks are mounted on the buccal sidewall of the posterior portion of said upper splint, and wherein said ends of said traction bow are mounted on the buccal sidewall of the posterior portion of said lower splint.

13. The orthodontic appliance of claim 7, wherein said traction bow includes a plurality of hooks on a forward portion thereof.

14. The orthodontic appliance of claim 7, wherein said traction bow includes a sub bar fixed to a frontal center portion thereof, said sub bar having a pair of laterally spaced ends extending above said frontal center portion of said traction bow.

15. The orthodontic appliance of claim 7, wherein said splints each include a plurality of sockets for individual teeth and filling interdental space.

16. The orthodontic appliance of claim 7, wherein said splints each include a buccal sidewall at least on a posterior portion thereof, and wherein said upper splint includes a pair of traction hooks mounted on the buccal sidewall of the posterior portion thereof, and wherein said traction bow includes two ends mounted on the buccal sidewall of the posterior portion of said lower splint.

17. A method of treating Class III malocclusion, comprising:
   forming an upper splint for removable attachment to a patient's upper set of teeth;
   forming a lower splint for removable attachment to a patient's lower set of teeth;
   interconnecting said upper and lower splints with at least one elastic traction element so as to exert a forward pulling force on said upper splint relative to said lower splint; and
   placing said upper and lower splints onto the patient's upper and lower sets of teeth, respectively.

18. The method of claim 17, further comprising:
   mounting a pair of traction hooks on said upper splint for attachment of a pair of elastic traction elements thereto; and,
   connecting a traction bow to said lower splint, said traction bow having a sub bar fixed to the frontal center thereof,
      wherein said interconnecting step comprises attaching an elastic traction element between each of said traction hooks and a respective end of said sub bar.

19. The method of claim 18, wherein said interconnecting is performed with rubber bands.

20. The method of claim 19, wherein said traction hooks are mounted on a posterior portion of said upper splint and said traction bow is connected to a posterior portion of said lower splint.

21. An orthodontic appliance for the treatment of a Class III malocclusion, comprising:
   a traction bow having a bowed bar and a sub bar of substantially shorter length than said bowed bar fixed to the frontal center of said bowed bar;
   a first upper anchor retentive to an upper set of teeth and attachable thereto and removable therefrom by a patient;
   a second lower anchor, which accomodates said bowed bar, retentive to a lower set of teeth and attachable thereto and removable therefrom by a patient; and
   at least one elastic traction element attached between said first and second anchors.

22. An orthodontic appliance for the treatment of a Class III malocclusion, comprising:
   an upper splint retentive to an upper set of teeth and attachable thereto and removable therefrom by a patient;
   a lower splint retentive to a lower set of teeth and attachable thereto and removable therefrom by a patient; and
   at least one elastic traction element attached between said upper and lower splints which exerts forward pulling force on said upper splint relative to said lower splint, wherein said upper splint is adapted to be mounted above said lower splint and in contact therewith in a plane generally parallel to the occlusal plane of the patient's upper set of teeth.

23. The orthodontic appliance of claim 22, further comprising:

a pair of traction hooks fixed to said upper splint, and;

a bowed bar having two ends connected to said lower splint and a sub bar fixed to the frontal center of said bowed bar and having two laterally spaced ends, an elastic traction element attached between each of said traction hooks on said upper splint and wherein said at least one elastic traction element comprises at least one end of said sub bar.

24. The orthodontic appliance of claim 23, wherein said elastic traction elements are rubber bands.

25. The orthodontic appliance of claim 24, wherein each traction hook is fixed to a posterior portion of said upper splint and each end of said bowed bar is connected to a posterior portion of said lower splint.

26. The orthodontic appliance of claim 22, wherein each said elastic traction element is a rubber band.

27. The orthodontic appliance of claim 22, wherein each said elastic traction element is attached to a posterior portion of said upper splint and extends forward therefrom at an angle inferior to the occlusal plane of the patient's upper set of teeth when said appliance is worn by the patient.

28. A method of treating Class III malocclusion, comprising:

forming an upper splint for removable attachment to a patient's upper set of teeth;

forming a lower splint for removable attachment to a patient's lower set of teeth;

interconnecting said upper and lower splints with at least one elastic traction element so as to exert a forward pulling force on said upper splint relative to said lower splint; and placing said upper and lower splints onto the patient's upper and lower sets of teeth, respectively, such that said upper splint is mounted above said lower splint and in contact therewith in a plane generally parallel to the occlusal plane of the patient's upper set of teeth.

29. The method of claim 28, further comprising:

mounting a pair of traction hooks on said upper splint for attachment of a pair of elastic traction elements thereto; and connecting a traction bow to said lower splint, said traction bow having a sub bar fixed to the frontal center thereof, wherein said interconnecting step comprises attaching an elastic traction element between each of said traction hooks and a respective end of said sub bar.

30. The method of claim 28, wherein said interconnecting is performed with rubber bands.

31. An orthodontic appliance for the treatment of a Class III malocclusion, comprising:

an upper splint retentive to an upper set of teeth and attachable thereto and removable therefrom by a patient;

a lower splint retentive to a lower set of teeth and attachable thereto and removable therefrom by a patient;

at least one traction hook fixed to a posterior portion of said upper splint;

a bowed bar having two ends connected to said lower splint; and an elastic traction element attached betweeen each said traction hook on said posterior portion of said upper splint and an anterior portion of said bowed bar.

32. The orthodontic appliance of claim 31, wherein each said elastic traction element is a rubber band.

33. The orthodontic appliance of claim 31, wherein each said elastic traction element extends forward from said posterior portion of said upper splint at an angle inferior to the occlusal plane of the patient's upper set of teeth when said appliance is worn by the patient.

* * * * *